(12) United States Patent
Mazzocca et al.

(10) Patent No.: US 9,186,432 B2
(45) Date of Patent: Nov. 17, 2015

(54) HIGH STRENGTH SUTURE COATED WITH COLLAGEN

(75) Inventors: Augustus D. Mazzocca, West Hartford, CT (US); MaryBeth McCarthy, Kensington, CT (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 13/524,780

(22) Filed: Jun. 15, 2012

(65) Prior Publication Data

US 2012/0259360 A1    Oct. 11, 2012

Related U.S. Application Data

(63) Continuation of application No. 11/845,670, filed on Aug. 27, 2007, now abandoned.

(60) Provisional application No. 60/840,466, filed on Aug. 28, 2006.

(51) Int. Cl.
| | |
|---|---|
| *A61B 17/04* | (2006.01) |
| *B05D 1/18* | (2006.01) |
| *A61L 17/14* | (2006.01) |
| *A61L 17/04* | (2006.01) |
| *D04C 1/02* | (2006.01) |
| *C08L 23/06* | (2006.01) |

(52) U.S. Cl.
CPC .............. *A61L 17/145* (2013.01); *A61L 17/04* (2013.01); *D04C 1/02* (2013.01); *B05D 1/18* (2013.01); *C08L 23/06* (2013.01); *C08L 2203/12* (2013.01); *D10B 2509/04* (2013.01)

(58) Field of Classification Search
CPC .................. A61B 17/06166; A61L 17/145

USPC ................ 427/2.31, 430.1; 606/228–229
See application file for complete search history.

(56) References Cited

U.S. PATENT DOCUMENTS

| | | | |
|---|---|---|---|
| 1,254,031 A * | 1/1918 | Davis ........................... 606/229 |
| 2,934,447 A * | 4/1960 | Highberger et al. ........ 106/124.6 |
| 3,034,852 A * | 5/1962 | Nishihara ..................... 264/202 |
| 3,276,448 A | 10/1966 | Kronenthal |
| 3,808,113 A * | 4/1974 | Okamura ....................... 427/493 |
| 3,942,532 A | 3/1976 | Hunter et al. |
| 3,949,755 A | 4/1976 | Vaquois |
| 4,047,533 A | 9/1977 | Perciaccante et al. |
| 4,321,038 A | 3/1982 | Porteous |
| 4,344,908 A | 8/1982 | Smith et al. |
| 4,411,854 A | 10/1983 | Maurer et al. |
| 4,422,993 A | 12/1983 | Smith et al. |
| 4,430,383 A | 2/1984 | Smith et al. |
| 4,436,689 A | 3/1984 | Smith et al. |
| 4,668,717 A | 5/1987 | Lemstra et al. |
| 5,019,093 A | 5/1991 | Kaplan et al. |
| 5,067,538 A | 11/1991 | Nelson et al. |

(Continued)

FOREIGN PATENT DOCUMENTS

| | | |
|---|---|---|
| EP | 1 293 218 A1 | 3/2003 |
| WO | WO 2006/062342 A1 | 6/2006 |

*Primary Examiner* — Cachet Sellman
(74) *Attorney, Agent, or Firm* — Dickstein Shapiro LLP

(57) ABSTRACT

A high strength surgical suture formed of ultrahigh molecular weight polyethylene (UHMWPE) yarns, the suture being coated with native or denatured collagen. The braided jacket surrounds a core formed of twisted yarns of ultrahigh molecular weight polyethylene. The suture has exceptional strength, is ideally suited for most orthopedic procedures, and can be attached to a suture anchor or a curved needle.

9 Claims, 2 Drawing Sheets

(56) References Cited

U.S. PATENT DOCUMENTS

| | | |
|---|---|---|
| 5,234,764 A | 8/1993 | Nelson et al. |
| 5,261,886 A | 11/1993 | Chesterfield et al. |
| 5,314,446 A | 5/1994 | Hunter et al. |
| 5,318,575 A | 6/1994 | Chesterfield et al. |
| 5,383,925 A | 1/1995 | Schmitt |
| 5,403,659 A | 4/1995 | Nelson et al. |
| 5,540,703 A | 7/1996 | Barker, Jr. et al. |
| 5,630,976 A | 5/1997 | Nelson et al. |
| 5,720,765 A | 2/1998 | Thal |
| 5,891,167 A * | 4/1999 | Totakura ............... 606/229 |
| 6,045,571 A | 4/2000 | Hill et al. |
| 6,063,105 A | 5/2000 | Totakura |
| 6,716,234 B2 | 4/2004 | Grafton et al. |
| 7,029,490 B2 | 4/2006 | Grafton et al. |
| 2003/0050667 A1* | 3/2003 | Grafton et al. ............ 606/228 |
| 2004/0033249 A1* | 2/2004 | Sewing et al. ............ 424/423 |
| 2005/0033362 A1 | 2/2005 | Grafton |

* cited by examiner

200
HIGH STRENGTH SUTURE COATED WITH COLLAGEN

CROSS-REFERENCE TO RELATED APPLICATIONS

This application is a continuation of application Ser. No. 11/845,670, filed Aug. 27, 2007, now abandoned, the entirety of which is incorporated herein by reference.

This application claims priority to U.S. Provisional Application No. 60/840,466, filed on Aug. 28, 2006, the entire disclosure of which is hereby incorporated by reference.

BACKGROUND OF THE INVENTION

1. Field of the Invention

The present invention relates to high strength surgical suture materials, and more particularly to braided suture blends of ultrahigh molecular weight polyethylene having bioabsorbable coatings.

2. Description of the Related Art

Suture strength is an important consideration in any surgical suture material. One of the strongest materials currently formed into elongated strands is an ultrahigh molecular weight long chain polyethylene, typically used for fishing line and the like, which is sold under the trade names Dyneema or Spectra. This material is much stronger than ordinary surgical suture, however, it does not have acceptable knot tie down characteristics for use in surgical applications.

BRIEF SUMMARY OF THE INVENTION

The present invention advantageously provides a high strength surgical suture material with improved tie down characteristics. The suture features a braided jacket made of ultrahigh molecular weight fibers coated with collagen. The ultrahigh molecular weight polyethylene provides strength. Polyester fibers woven with the high molecular weight polyethylene provide improved tie down properties. Collagen coating is provided to stimulate proliferation and protein synthesis more than standard sutures, and therefore may aid in the tendon-to-bone incorporation process. Moreover, collagen, in addition to providing structural support, can interact with other matrix proteins and cellular receptor affecting cell behavior and gene expression.

There are 19 recognized genetically distinct collagen types and amongst them, the most abundant type is the collagen type I, a heterotrimer. Integrins, a heterodimeric cell surface receptor involved in cell-cell and cell-substrate adhesion, bind the collagen. Typically, four different integrins, for example, $\alpha_1\beta_1$, $\alpha_1\beta_1$, $\alpha_{10}\beta_1$ and $\alpha_{11}\beta_1$, are required to bind a collagen. The interactions of integrins with collagen involve a von Willebrand factor A-like domain and require triple helical collagen structures.

Many of the integrins can react with a specific amino acid sequence. Certain integrins appear to bind to only one specific ligand such as a fibronectin receptor, whereas other integrins such as platelet IIb/IIIa and vitronectin receptor can interact with numerous Arg-Gly-Asp (RGD)-containing proteins. Although collagens contain RGD sequences in their primary sequences, the RGD sequences are cryptic and generally inaccessible to cells in the native proteins and therefore, collagens are considered as non-RGD-dependent ligands.

In a preferred embodiment, the suture includes a multifilament jacket formed of ultrahigh molecular weight polyethylene fiber braided with polyester. The jacket surrounds a fiber core made substantially or entirely of ultrahigh molecular weight polyethylene. The core preferably includes three strands of ultrahigh molecular weight polyethylene, twisted at about three to six twists per inch.

The jacket preferably comprises eight strands of ultrahigh molecular weight polyethylene braided with six strands of polyester. Tinted strands can be included in black or some other contrasting color.

Ultrahigh molecular weight polyethylene fibers suitable for use in the present invention are marketed under the Dyneema trademark by Toyo Boseki Kabushiki Kaisha, and are produced in the U.S. by Honeywell under the trademark Spectra.

The suture of the present invention advantageously has the strength of Ethibond No. 5 suture, yet has the diameter, feel and tie-ability of No. 2 suture. As a result, the suture of the present invention is ideal for most orthopedic procedures such as rotator cuff repair, Achilles tendon repair, patellar tendon repair, ACL/PCL reconstruction, hip and shoulder reconstruction procedures, and replacement for suture used in or with suture anchors.

The suture is coated with collagen. Collagen suitable for use in the present invention is marketed under the FIBRACOL trademark by Johnson & Johnson, Medifil® by BioCore, and hyCURE® by The Hymed Group.

A trace thread or two in the suture jacket aids surgeons in identifying the travel direction of the suture during surgery, particularly during operations viewed arthroscopically or remotely. Providing the trace threads in a regularly repeating pattern is particularly useful, allowing the surgeon to decode different ends of a length of suture, and to determine the direction of travel of a moving length of suture. The trace threads preferably are provided uniquely on each half of a length of suture to allow for tracing and identification of each end of the suture, such as when the suture is threaded through an eyelet of a suture anchor.

Other features and advantages of the present invention will become apparent from the following description of the invention which refers to the accompanying drawings.

DETAILED DESCRIPTION OF THE INVENTION

The term "yarn(s)," as used herein, is to be understood as including fiber(s), filament(s), and the like used to make a suture of the present invention. Typically, though, yarns are comprised of fibers and/or filaments.

Figure 1:
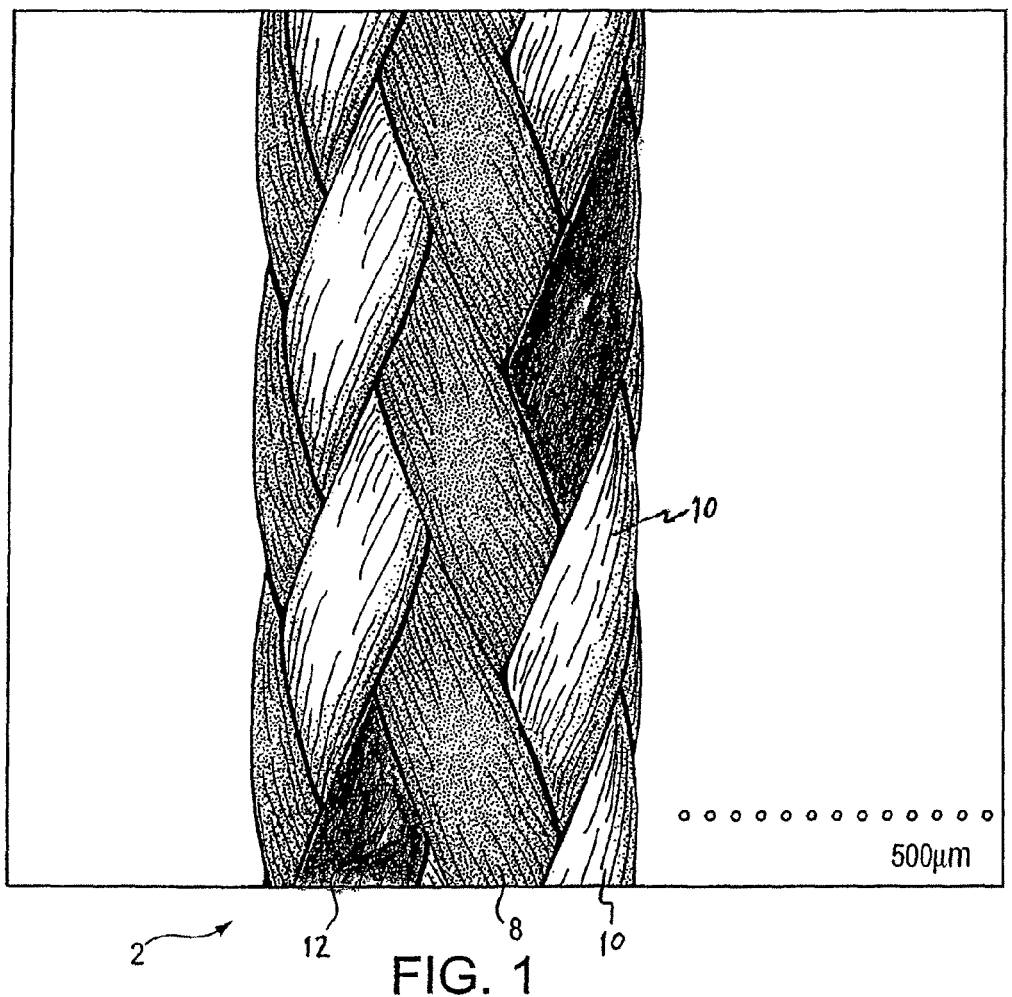
FIG. 1 is a copy of a scanning electron micrograph of a length of suture according to the present invention.
Figure 2:
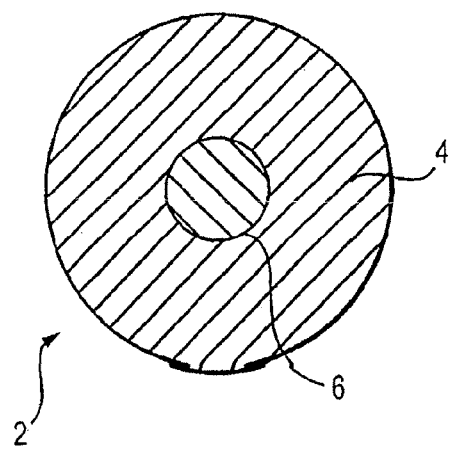
FIG. 2 is a schematic cross section of a length of suture according to the present invention.

Referring to FIG. 1, a scanning electron micrograph of a length of suture 2 according to the present invention is shown. Suture 2 is made up of a jacket 4 and a core 6 surrounded by the jacket 4. See FIG. 2. Strands of ultrahigh molecular weight polyethylene (UHMWPE) 8, such as that sold under the tradenames Spectra and Dyneema, strands of polyester 10, and tinted strands 12 are braided together to form the jacket 4. Core 6 is formed of twisted strands of UHMWPE.

UHMWPE, used for strands 8, is substantially translucent or colorless. The polyester strands 10 are white (undyed). Due to the transparent nature of the UHMWPE, the suture takes on the color of strands 10 and 12, and thus appears to be white with a trace in the contrasting color.

In accordance with the present invention, trace strands 12 are preferably provided in black. The black trace assists surgeons in distinguishing between suture lengths with the trace and suture lengths without the trace. Traces also assist the surgeon in identifying whether the suture is moving. The trace can extend the entire length of the suture or only on half of a length of suture, the other half of the suture length remaining plain (white). Alternatively, the traces can form visibly distinct coding patterns on each half of the suture length. As a result, when the suture is threaded through the eyelet of a suture anchor, for example, the two legs (halves) of the length of suture are easily distinguished, and their direction of travel will be readily evident when the suture is pulled during surgery.

Details of the present invention will be described further below in connection with the following examples:

EXAMPLE

USP Size 5 (EP size 7)

Made on a 16 carrier Hobourns machine, the yarns used in the braided jacket are Honeywell Spectra 2000, polyester type 712, and nylon. The jacket is formed using eight strands of 144 decitex Spectra per carrier, braided with six strands of 100 decitex polyester, and two strands of tinted nylon. The core is formed of three carriers of 144 decitex Spectra braided at three to six twists per inch. A No. 5 suture is produced.

To make various sizes of the inventive suture, different decitex values and different PPI settings can be used to achieve the required size and strength needed. In addition, smaller sizes may require manufacture on 12 carrier machines, for example. The very smallest sizes can be made without a core. Overall, the suture may range from 5% to 90% ultrahigh molecular weight polymer (preferably at least 40% of the fibers are ultrahigh molecular weight polymer), with the balance formed of polyester and/or nylon. The core preferably comprises 18% or greater of the total amount of filament.

The suture is coated with collagen (FIBRACOL, Medifil), a bioabsorbable material. Collagen is a natural biomaterial that acts as a hemostatic agent. Collagen coating, like all suture coatings, also improves the pliability and handleability of the suture without sacrificing the physical properties of the constituent elements of the suture.

In one embodiment of the present invention, a suture may be coated with native collagen. First, suitable amounts of collagen are dissolved in acetic acid of about 0.1% concentration to derive a stock solution having a final concentration of about 0.5 mg/ml. The stock solution is further diluted with water to a final concentration of about 0.5 mg/ml and the suture is soaked in the stock solution at 4° C. The suture is then dried for at least 1 hour in a laminar flow hood free of dust and debris. About 30 mg of collagen can coat about 200 ft of the suture. A collagen-coated suture may be stored at room temperature for future use.

In yet another embodiment of the present invention, a suture may be coated with denatured collagen. First, suitable amounts of collagen are dissolved in acetic acid of about 0.1% concentration to derive a stock solution having a final concentration of about 0.5 mg/ml. The stock solution is then heated in a water bath at about 50° C. for about 12 hours, later diluted with water to about 0.5 mg/ml and the suture soaked at 4° C. The suture is then dried for at least 1 hour in a laminar flow hood free of dust and debris. About 30 mg of collagen can coat about 200 ft of the suture. A collagen-coated suture may be stored at room temperature for future use.

In an alternative embodiment of the present invention, a partially bioabsorbable suture is provided by blending a high strength material, such as UHMWPE fibers, with a bioabsorbable material, such as PLLA or one of the other peptides, for example. Accordingly, a suture made with about 10% Spectra or Dyneema blended with absorbable fibers would provide greater strength and with less stretch. Over time, 90% or more of the suture would absorb, leaving only a very small remnant of the knot. The absorbable suture can include coatings, for example collagen.

The ultra high molecular weight (UHMW) polymer component of the present invention provides strength, and the polyester component is provided to improve tie ability and tie down characteristics. However, it has been found that the UHMW polymer provides an unexpected advantage of acting as a cushion for the polyester fibers, which are relatively hard and tend to damage each other. The UHMW polymer prevents breakage by reducing damage to the polyester when the suture is subjected to stress.

Figure 3:
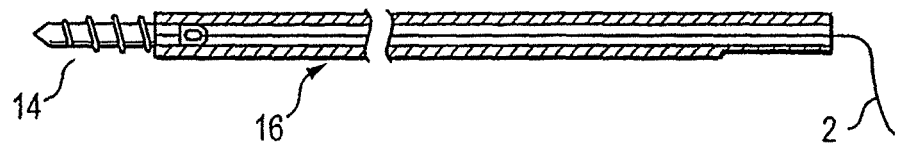
FIG. 3 is an illustration of the suture of the present invention attached to a suture anchor loaded onto a driver.
Figure 4A:
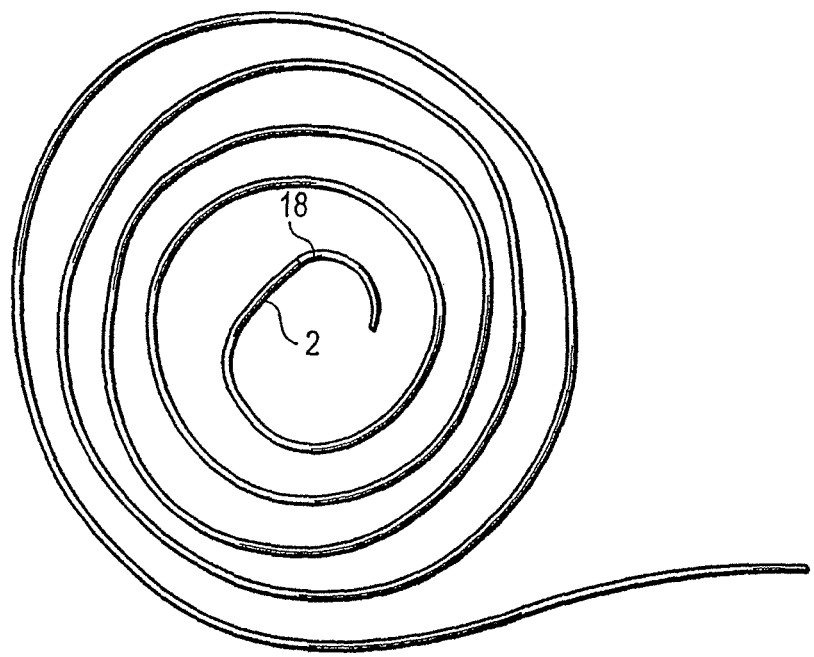
FIGS. 4A and 4B show the suture of the present invention attached to a half round, tapered needle.
Figure 4B:
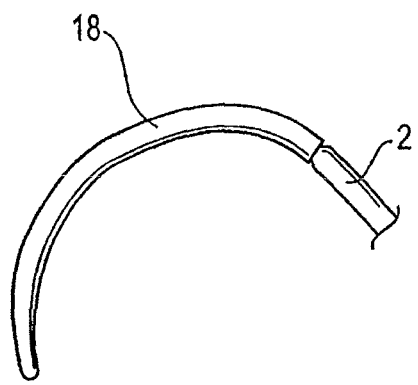

In one method of using the suture of the present invention, the suture 2 is attached to a suture anchor 14 as shown in FIG. 3 (prepackaged sterile with an inserter 16), or is attached at one or both ends to a half round, tapered needle 18 as shown in FIGS. 4A and 4B. FIG. 4A also illustrates a length of suture having regularly repeating pattern of trace threads according to the present invention. Sections of the length of suture 2 have tinted tracing threads woven in. The alternating patterned and plain sections aid the surgeon in determining the direction of suture travel when pulling the suture, for example.

Although the present invention has been described in relation to particular embodiments thereof, many other variations and modifications and other uses will become apparent to those skilled in the art.

What is claimed is:

1. A method of making a non-absorbable, high strength suture comprising a jacket comprising a plurality of braided untreated multi-filament yarns formed of ultrahigh molecular weight polyethylene, the suture being coated with native collagen, consisting of the steps of:
   dissolving native collagen in an acidic solution of acetic acid of about 0.1% concentration to form a stock solution of dissolved native collagen, wherein stock solution of dissolved native collagen has a final concentration of about 0.5 mg/ml;
   further diluting the stock solution of dissolved native collagen with water to obtain a diluted solution of dissolved native collagen;
   soaking the braided untreated suture in the diluted solution of dissolved native collagen at a temperature of 4° C. to coat the braided suture with native collagen;
   drying for about 1 hour the braided suture soaked with native collagen to reduce moisture content of the collagen and obtain a collagen-coated suture with a collagen coating, the collagen coating stimulating proliferation and protein synthesis and providing structural support to the collagen-coated suture; and
   storing the collagen-coated suture at room temperature for future use, wherein the jacket comprises yarns of the ultrahigh molecular weight polyethylene braided with yarns of polyester.

2. The method of claim 1, wherein the suture further comprises a core comprising yarns of ultrahigh molecular weight polyethylene surrounded by the jacket.

3. The method of claim 2, wherein the yarns of ultrahigh molecular weight polyethylene comprise at least 40% of the yarns in the suture.

4. The method of claim 2, wherein the core comprises about 18% or greater of the total amount of yarns in the suture.

5. The method of claim 2, wherein the jacket further comprises trace yarns for suture identification.

6. The method of claim 2, wherein the core is formed of at least three yarns of the ultrahigh molecular weight polyethylene twisted at three to six twists per inch.

7. The method of claim 2, wherein the jacket comprises at least eight yarns of the ultrahigh molecular weight polyethylene braided with six yarns of polyester and two yarns of nylon.

8. The method of claim 1, further comprising the step of attaching the collagen coated suture to a suture anchor.

9. The method of claim 1, further comprising the step of attaching the collagen coated suture to a needle.

\* \* \* \* \*